United States Patent [19]

Bimberg et al.

[11] 4,429,999
[45] Feb. 7, 1984

[54] METHOD FOR CALORIMETRIC ABSORPTION SPECTROSCOPY AND DEVICE FOR WORKING THE METHOD

[76] Inventors: Dieter H. Bimberg, von Broich-Str. 6, D-510 Aachen; Achim Bubenzer, Markenhofstr. 9, D-7815 Kirchzarten/Burg; Klaus F. K. Dransfeld, Sperberweg 23, 703 Böblingen; Siegfried Hunklinger, Steinhöwelstr. 8, 7252 Weil d. Stadt, all of Fed. Rep. of Germany

[21] Appl. No.: 276,181

[22] Filed: Jun. 22, 1981

[51] Int. Cl.³ .......................................... G01N 21/00
[52] U.S. Cl. .................................. 356/432; 250/341; 356/73.1; 374/32
[58] Field of Search ............... 356/432, 73.1; 250/341; 374/32, 45

[56] References Cited

U.S. PATENT DOCUMENTS 4,041,313  8/1977  Potter et al. ........................ 356/432
4,185,497  1/1980  Decker et al. ........................ 374/32

OTHER PUBLICATIONS

Cohen et al., "Loss Measurements in Optical Fibers, 2: Bolometric Measuring Instrumentation" *Applied Optics*, vol. 13, No. 11 (Nov. 1974), pp. 2522–2524.

Primary Examiner—R. A. Rosenberger
Attorney, Agent, or Firm—Antonelli, Terry & Wands

[57] ABSTRACT

A method of calorimetric absorption spectroscopy (CAS) is claimed, wherein a sample, irradiated with a measuring-light pulse of a specified power, duration, and wavelength and whose absorbance at the specific wavelength of the measuring light is determined as a result of the heating of the sample which occurs as a result of the absorption of a portion of the measuring light, is cooled to a temperature which is so low that the specific heat of the sample during measurement is only a small fraction of the value at normal temperature. This produces an increase in sensitivity by a factor of more than $10^5$. The manner in which the lifetime of radiant and nonradiant recombination can be determined in a simple fashion is claimed for samples which have a first impurity center, capable of recombination both by radiation and without radiation, and a second center, capable of recombination only without radiation. The temperature sensor in the sample chamber is placed in a cryostat suitable for working the method, and shielded hermetically against the measuring light and the scattered light resulting from the latter.

11 Claims, 4 Drawing Figures

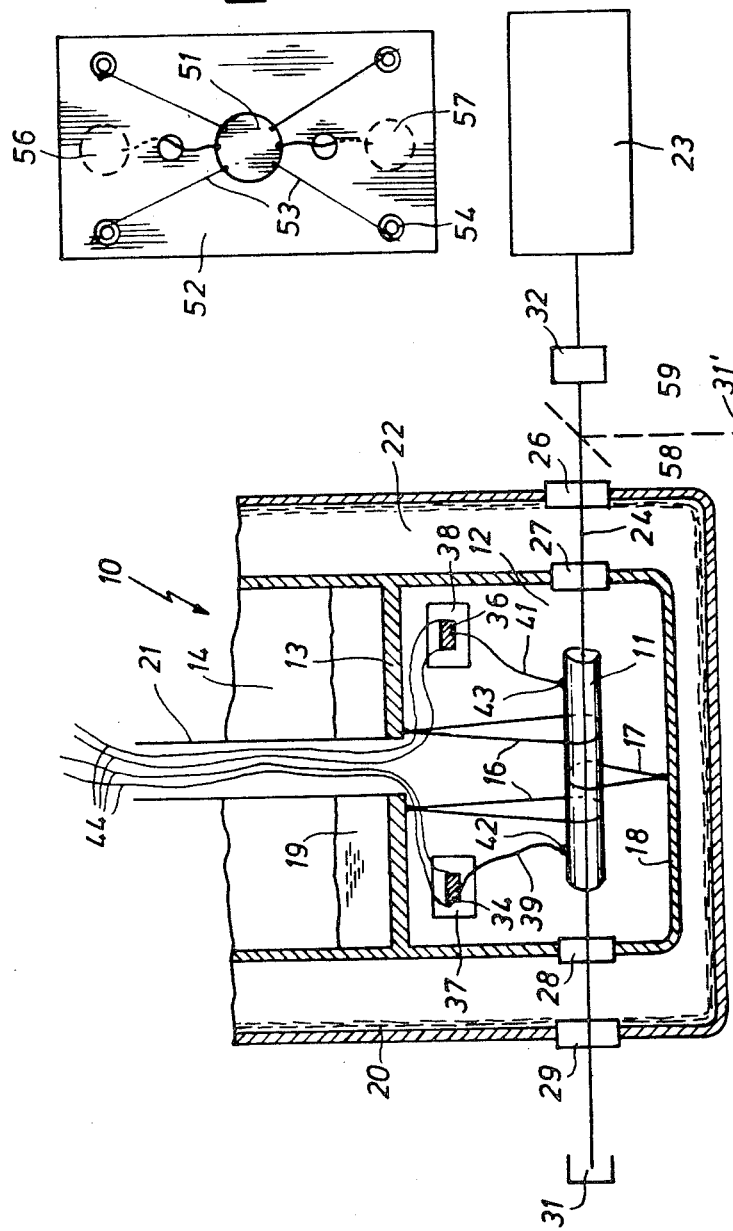

METHOD FOR CALORIMETRIC ABSORPTION SPECTROSCOPY AND DEVICE FOR WORKING THE METHOD

The invention relates to a method for calorimetric absorption spectroscopy, wherein a sample is irradiated with a measuring-light pulse of a specific power, duration, and wavelength, and the absorbance of the sample at the specific wavelength of the measuring light is determined as a function of the heating of the sample which occurs as a consequence of absorption of a portion of the measuring light.

BACKGROUND OF THE INVENTION

Glasses with extremely low absorption coefficients are available today for manufacturing optical fibers for data transmission and it is extremely valuable from the technical standpoint to know the basic absorption of such glasses, whose loss behavior can change when they are processed into optical fibers. Thus, a method is required which makes it possible to determine, as exactly as possible, extremely low optical absorption coefficients with typical values of 1 dB km$^{-1}$ (2.3·10$^{-6}$ cm$^{-1}$). A similar problem arises in studying recombination processes in solids, wherein charge carriers are present, bonded to lattice defects or to impurity atoms incorporated in the lattice, the electronic excitation states of said carriers being occupied by resonant excitation with monochromatic light and can recombine emitting photons (radiant recombination or luminescence) and/or phonons (nonradient recombination). A serious problem here is the detection of the portion of the exciting-light power which is consumed in phonon emission, in order to determine the quantum yield of the luminescence radiation.

In both cases, a small amount of absorption must be determined as accurately as possible, either because the characteristic absorption coefficients are very low or because only thin-layer thicknesses of the materials under study are available and/or the charge carrier concentration is low.

State of the Art

Material absorption can be determined using the generally known method of optical transmission measurement, involving determination of absorbance as the result of the attenuation of the intensity of a measuring-light flux conducted through the sample. An important disadvantage of this method is that when the absorption coefficients of the sample material are low, considerable sample layer thicknesses are required so that even when a highly developed special spectrophotometer is used, highly elongated samples with a typical length of approximately 30 cm may be necessary to provide a layer thickness required for a specific measuring accuracy; cf. for example D. Krause, "Optical Properties of Highly Transparent Solids," edited by S. S. Mitra and B. Bendow (Plenum, New York, 1975), p. 483. This fact alone imposes drastic limitations on the possible applications of the transmission measurement method, since samples with the required layer thicknesses can be provided only within a limited class of sample materials.

Another, basic disadvantage of the transmission measurement method is that reflection and scattering losses must be taken into account as well, and their determination requires additional measurements which often entail considerable errors.

If we use $I_0$ and $I_t$ to represent the intensities of the light fluxes entering and leaving the sample, $t_1$ and $t_2$ to represent the transmission coefficients of the sample at the entry and exit points of the light, $\alpha$ to represent the absorption coefficient of the sample material, and d to represent its thickness, if we disregard multiple reflections between the entry and exit points, the relative error $\Delta\alpha/\alpha$, with which the absorption coefficient $\alpha$ can be determined from a transmission measurement will be as follows:

$$\frac{\Delta\alpha}{\alpha} = \frac{1}{\alpha d}\left(\left|\frac{\Delta I_t}{I_t}\right| + \left|\frac{\Delta I_0}{I_0}\right| + \left|\frac{\Delta t_1}{t_1}\right| + \left|\frac{\Delta t_2}{t_2}\right|\right) \quad (1)$$

We can see from the above that the relative error in $\alpha$ increases inversely with $\alpha d$ and will be on the order of 100% for the case in which $I_t$, $I_0$, $t_1$, and $t_2$ have errors of 1% each and the sample has a relatively high absorption coefficient of, for example, 600 dB/km and the layer thickness d is 30 cm.

Hence, transmission measurements are no longer suitable for determining small absorption coefficients $\alpha$ of, for example 10 dB/km or less, at reasonable sample thicknesses or lengths.

It is also known that the absorption coefficient $\alpha$ of a sample can be determined by calorimetric measurement of the energy Q acquired through absorption, said energy, when the sample is irradiated with a light pulse with intensity $I_0$, wavelength $\lambda$, and duration $\Delta t$, being given by the relationship $$Q = \frac{I_0(1-R)(1-\exp(-\alpha d))\Delta t}{1 - R \cdot \exp(-\alpha d)} \quad (2)$$

where $\alpha(\lambda)$ is the wavelength-dependent absorption coefficient, d is the layer thickness of the sample and R is the reflection coefficient of the latter. Then, for $\alpha \cdot d \ll 1$ we will have with a very good approximation $$Q = I_0 \cdot \alpha \cdot d \cdot \Delta t \quad (3)$$

The relative error $$\frac{\Delta\alpha}{\alpha}$$

is then given, likewise in good approximation, by the relationship $$\frac{\Delta\alpha}{\alpha} = \left|\frac{\Delta Q}{Q}\right| + \left|\frac{\Delta I_0}{I_0}\right| + \left|\frac{\Delta d}{d}\right| + \left|\frac{\Delta(\Delta t)}{\Delta t}\right| \quad (4)$$

where the sum of the individual errors with reasonable sample dimensions can generally be kept much lower, by suitable dimensioning of the calorimeter and with a sufficiently high light intensity and duration of the measuring light pulse, than in the case of the abovementioned transmission measurement. However, it is often necessary to use high-powered lasers as light sources in order to be able to keep the critical errors $$\frac{\Delta Q}{Q} \text{ and } \frac{\Delta I_0}{I_0}$$

for measurement low, but such lasers are available only for discrete wavelengths of light, so that in such cases the precise wavelength dependence of the absorbance cannot be measured.

The same is essentially true of the photoacoustic spectroscopic method (PAS) which is partially in competition with the CAS method. According to the PAS method, the sample is exposed to radiation by a pulsed light flux and its heating and consequently its absorbance are determined by the noise power picked up by a microphone which in turn is in sonic contact through a carrier gas with the sample, which expands in rhythm with the irradiation (cf. for example, A. Rosencwaig, *Advances in Electronics and Electron Physics*, Vol. 46, p. 207, L. Marbon, editor, Academic Press, 1978, as well as C. K. N. Patell, A. C. Tamm in *Appl. Phys. Letters*, Vol. 36, p. 7, 1980).

In the versions known thus far, both calorimetric absorption spectroscopy and photoacoustic absorption spectroscopy, the lowest measurable absorption coefficients are approximately $10^{-5}$ cm$^{-1}$, but this sensitivity, as we have already mentioned, requires the use of high-power lasers as light sources.

BRIEF DESCRIPTION OF THE INVENTION

Hence, the goal of the invention is to provide a method of absorption measurement which will function at the preset measurement accuracy with much smaller values for the minimum detectable light power, so that continuously variable light sources, operating with relatively low light power outputs, can be used to excite the sample.

Using the CAS method cited hereinabove as a basis, this problem is solved in a simple fashion according to the invention by the features listed in the characterizing clause of claim 1.

According to this claim, the sample is cooled in a suitable cryostat until its specific heat is only a small fraction of the value at normal temperature.

The resultant advantages of the method according to the invention are at least the following:

The measuring sensitivity is increased at least by the factor by which the specific heat can be reduced. If the sample is cooled to a temperature which is approximately 1/100th of its Debye temperature $\theta$, because of the then valid $t^3$ dependence of the specific heat, values for the latter can easily be reached which are only $10^{-4}$ to $10^{-5}$ times the value at normal temperature, whereby the sensitivity is increased by a factor of $10^4$ to $10^5$. By comparison with the known versions of the CAS and PAS methods, therefore, the method according to the invention can use light sources whose light power at the output is only a $10^{-4}$ to $10^{-5}$ fraction of the light power that would otherwise be necessary, i.e., conventional lamps can be used as light sources in conjunction with high-resolution monochromators, whereby the continuously usable wavelength range is not subject to any theoretical limitations whatever and can extend from the ultraviolet to far in the infrared spectrum, and possibly into the microwave range. Another important advantage is that a single temperature sensor can be used over the entire measuring and wavelength range to detect the increase in the sample temperature which results from radiation absorption, and the heat generated in the sample can then be determined from this temperature rise.

In order to achieve the increase in sensitivity which is characteristic of the method according to the invention, it is of advantage to cool the sample to a temperature which is as close as possible to absolute zero, whereby it is sufficient for practical applications to cool the sample to approximately 1.5 K. to 0.3 K., which can easily be done by using currently available He$^4$ or He$^3$ cyrostats, it being understood that slightly higher temperatures may be sufficient and slightly lower sample temperatures may be required, depending on the Debye temperature of the sample under investigation.

In order to achieve the most accurate measurement possible of the maximum temperature value $T_{max}$, reached by the sample as a consequence of radiation absorption, it is advantageous within a suitable time interval to record the temperature rise and sample temperature fall which occurs during irradiation and after decay of the measuring-light pulse, and to determine the abovementioned maximum by extrapolating the rising and falling parts of the temperature curve.

In order to achieve high sensitivity in temperature measurement, it is advantageous to measure the temperature curve using an NTC resistor, in good thermal contact with the sample surface, especially a carbon film resistor, whose resistance increases drastically at the abovementioned low temperatures, so that changes in sample temperature can be recorded very accurately. When such a carbon film resistor is used, having a resistance of about 500 ohms at room temperature (300 K.) and a resistance of about 50,000 ohms at 1.5 K., changes in resistance at this temperature can still be detected with sufficient accuracy.

In order to determine the absolute values of the amounts of heat developed in the sample from the measured sample temperatures and temperature curves, the sample is exposed to a specific quantity of heat in a reference measurement and the sample temperature (T) curve answer resulting from this addition of heat is recorded, and an absolute calibration is obtained from the comparison with the T curves resulting from radiation absorption.

The specific heating of the sample can be accomplished in simple fashion by using an electrical resistance heater.

The method according to the invention permits measurement of not only very small absorption coefficients, but is also especially suitable for absorption measurements on thin-film systems and also permits an accurate determination of quantum yields $\mu$ of recombination processes as well as the radiant and nonradiant lifetime of recombination processes if the method according to the invention is combined with measurements of the total lifetime of a specific excited state of an impurity center in a solid. It is advantageous in this connection if, in addition to an absorption spectrum of a solid, recorded by the method according to the invention, for example for a semiconductor having a first absorbent center, which recombines without radiation, i.e., with quantum yield $\mu=0$, and a second absorbent center, which recombines during resonant excitation by light absorption partially by photon emission (radiation) and partially by phonon emission (without radiation), as well as an absorption spectrum recorded by the transmission method. The comparison of the absorption bands measured in the transmission process can then be used to determine in simple fashion the ratio of the light power absorbed by the various centers and the comparison of the absorption maxima determined by the CAS method can be used to determine the amount which can be attributed to phonon emission in the center which recombines both with and without radiation. In one such special case, but one which is very frequent in practice, relative measurements alone suffice for absolute calibration of the CAS absorption spectrum and consequently an exact determination of the quantum yield. If the total lifetime $\tau_t$ of its excited state is also measured, for example by measuring the photon emission curve as a function of time for the center which recombines with and without radiation, the lifetimes of the radiant and nonradiant recombinations can be determined in simple fashion.

The subject of the invention includes an He cryostat suitable for working the method, said cryostat having an inner chamber to accept the sample, which is in good thermal contact with the coolant bath (liquid $He^4$ or $He^3$) and is fillable with gas (He) to accelerate sample cooling, said gas being pumped off as soon as the sample has been cooled to its low set temperature. This inner chamber is in turn located in a chamber which can likewise be evacuated to achieve good thermal insulation. The measuring light can be connected through windows in the outer chamber and sample chamber. A characteristic feature of the cryostat is that the temperature sensor, likewise located in the sample chamber, is located in the shadow of the measuring light in such fashion that the light does not strike the temperature sensor and therefore cannot undesirably heat the latter.

According to a preferred design for the cryostat, the sample holder is made in the form of a plate with good thermal conductivity, said plate being in direct thermal contact with the helium bath, whereby the sample is mounted with only slight thermal coupling to one side of the plate, and the temperature sensor is mounted on the other side of the plate with a similar poor thermal coupling to the sample holder, and whereby the thermal contact between the temperature sensor and the sample is produced by a copper wire with good thermal conductivity, said wire being guided to the sample through an opening in the sample holder plate.

DESCRIPTION OF PREFERRED EMBODIMENTS OF THE INVENTION

Drawing

Further details and features of the invention will be apparent from the following description of preferred embodiments of the method according to the invention, as well as devices suitable for its working.

FIG. 1 shows details of an He cryostat for performing calorimetric absorption measurements on an elongated quartz glass sample;

FIG. 2 is a diagram which is a qualitative representation of the time curve of the temperature curve response of the temperature sensor, when the sample has been irradiated by a light pulse of a specified wavelength, power, and duration;

Figure 3:
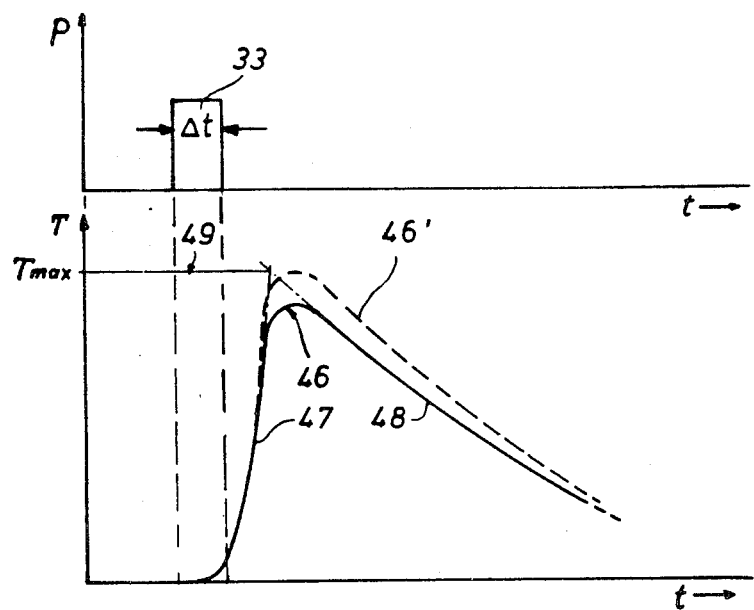
FIG. 3 shows details of a sample holder for plate-shaped samples with a small layer thickness.

Initially, FIG. 1 will be used to explain the structure of an He cryostat 10, with which absorption measurements using the CAS method according to the invention can be performed on a rod-shaped sample 11, approximately 5 cm long.

The cryostat has an inner, evacuable chamber 12, whose upper limiting wall 13 forms the bottom of supply chamber 14, wherein the coolant, $He^4$ or $He^3$ used as the cooling bath is located. The gas phase of a liquid coolant can be pumped off with the aid of a pumping system, not shown, to lower the boiling point of the coolant, so that when $He^4$ is used as a coolant, the lowest temperature that can be reached is approximately 1.1 K. while a temperature of approximately 0.3 K. can be used when $He^3$ is used as the coolant.

Sample 11 is suspended in the manner shown in FIG. 1 with the aid of thin nylon threads 16 and 17 from the cover 13 of sample chamber 12, and also attached to the bottom 18 of sample chamber 12. These nylon threads 16 and 17 allow only poor thermal coupling to the helium bath 19.

The sample chamber 12 can then be filled with helium gas through a central vertical pipe 21, said gas producing the good thermal contact with helium bath 19 needed to cool sample 11. This gas can be pumped off again by a pumping system, not shown, after sample 11 has reached a low temperature of approximately 1.5 K. suitable for measurement.

Sample chamber 12 in turn is located in an outer chamber 22, which can be evacuated to suppress effectively the conduction of heat from the outside to the inside.

Chamber 22 is provided on the inside with Super insulation 20, indicated by the dashed lines, said insulation being composed of a multilayer inner lining made of a thin plastic film, reflectorized, by evaporating aluminum on it, for example. Alternatively, or additionally, a radiation shield can be provided between inner chamber 12 and outer chamber 22, said shield being kept at the temperature of liquid nitrogen.

Outer chamber 22 and inner chamber 12 are provided with entrance windows 26 and 27 and exit windows 28 and 29 along the optical axis 24 of the complete system, marked by the lengthwise axis of the sample and the optical axis of a light source 23 used to irradiate the sample, through which windows the light emitted by light source 23 can enter cryostat 10 and sample 11 and the light absorbed by the latter can escape again from the cryostat and strike a radiation detector 31. The output signal of radiation detector 31 is a measure of the intensity $I_t$ of the light flux emerging from the sample; assuming weak absorption by the sample, the output signal of the radiation detector 31 can also be used to determine the intensity $I_0$ of the light flux striking sample 11, if the reflectance of the sample and that of cryostat windows 26 to 29 is known. This radiation detector 31 can also be used for making additional measurements by the transmission method. A shutter device 32 can be used to control the duration $\Delta t$ of measuring-light pulses 33 (FIG. 3), with which the sample is irradiated. In order to avoid undesirable heating of sample 11 by IR radiation from the environment, windows are used which are opaque to the undesirable IR radiation.

A first and a second carbon film resistor 34 and 36 are located in sample chamber 12, said resistors being hermetically shielded by radiation shields 37 and 38 against scattered light of any kind. The carbon film resistors 34 and 36 are connected with good thermal contact by copper wires 39 and 41 with the surface of sample 11, to which they are fastened by indium solder drops 42 and 43. Resistors 34 and 36 are located approximately 2 cm from sample 11. The two resistors 34 and 36 can be connected alternately to a resistance-measuring bridge, not shown, by thin constantan wires 44, whose thermal conductance is much lower than that of copper wires 39 and 41, by which the two carbon film resistors 34 and 36 are thermally coupled to sample 11. The resistance bridge can be used to measure accurately the resistance of whichever carbon film resistor 34 or 36 is connected to within approximately 0.1 ohm.

Consequently, changes in sample temperature of approximately $10^5$ K. can be measured conveniently by such a measurement of the resistance of carbon film resistor 34 or 36, which have a resistance of approximately 500 ohms at room temperature and a resistance of approximately $10^5$ ohms at 1.5 K.

As already mentioned at the outset, a conventional lamp connected in series with a high-resolution monochromator can be used as light source 23. However, it is more advantageous to use a dye laser as a light source, pumped by an argon-ion laser, in order to produce improved focusing conditions and to suppress false signals produced by scattered light.

When the sample is irradiated with a measuring-light pulse 33, with a duration Δt of approximately 1 second and a power of several mW, the energy absorbed by the sample produces heating of the sample and therefore also a heating of the carbon film resistors 34 and 36 which are in thermal contact with the sample, said heating being detected by the change in resistance of the resistor 34 or 38 connected in the measuring bridge. The voltage output signal produced by the change in resistance and the resultant tuning of the measuring bridge, whose changes as a function of time are represented by curve 46 in FIG. 2, is hence also a measure of the change in sample temperature with time as a function of the measuring-light pulse 33 conducted through the sample. A level 49 which can be determined, for example, by extrapolation of the rising branch 47 and the falling branch 48 is then a relative measure of the temperature increase Δt in sample 11 which results from light absorption and therefore also for the absorbed energy Q according to the relationship $$Q = mc\Delta t \qquad (5)$$

where m is the mass of the sample, and c is its specific heat.

An absolute calibration may be accomplished in simple fashion by applying a specific amount of heat Q' to the sample by applying a current pulse to one of the two resistors 34 or 36, and recording a temperature curve 46', indicated by the dashed lines in FIG. 3, analogous to curve 46, by using the other resistor 34 or 36, and then determining the calibration factor by comparison of curves 47 and 47'. In this way calibration is possible without knowing the values Δt, m, and c themselves.

For low values of the absorption coefficient (αd<<1), the absorption coefficient α can then be determined by the relationship $$\alpha = (Q/E_{in})d^{-1} \qquad (6)$$

where $E_{in}$ is the energy of the light pulse coupled to the sample, which, assuming small values of d, can also be determined from the light power received at detector 31 and the duration t of the measuring-light pulse. According to the method described above, even with a sample length of 1 cm, absorption coefficients of $10^{-8}$ cm$^{-1}$ or 0.004 dB km$^{-1}$ can still be measured conveniently using the device 10 shown in FIG. 1.

In order to perform similar measurements according to the CAS method of the invention on thin, e.g., plate-shaped samples 51, the plate-shaped sample holder 52 shown schematically in FIG. 3 can be used, for example which, in good thermal contact with helium bath 19, can be placed in the inner sample chamber 12 of a cryostat whose design is similar to the cryostat 10 shown in FIG. 1. Sample 51 is once again attached by nylon threads 53 to spacers 54 on sample holder plate 52. Resistors 56 and 57, represented by dashed lines and corresponding to carbon film resistors 34 and 36, are located on the side of sample holder 52, in the shadow of the measuring light, which is opposite sample 51. Moreover, the measuring system can be completely analogous to that shown in FIG. 1. In order to measure the intensity of the light beam striking the sample, as shown in FIG. 1, a fraction of the light flux 59, branched off from the input light flux by a beam splitter 58, can be used, said flux 59 being received by a radiation detector 31'. A measuring system thus modified does not require any exit windows 28 or 29 on the cryostat.

In order to suppress undesired scattered light, it is advantageous to provide a suitable sink which absorbs as much as possible of the radiation which passes through the sample.

Figure 4:
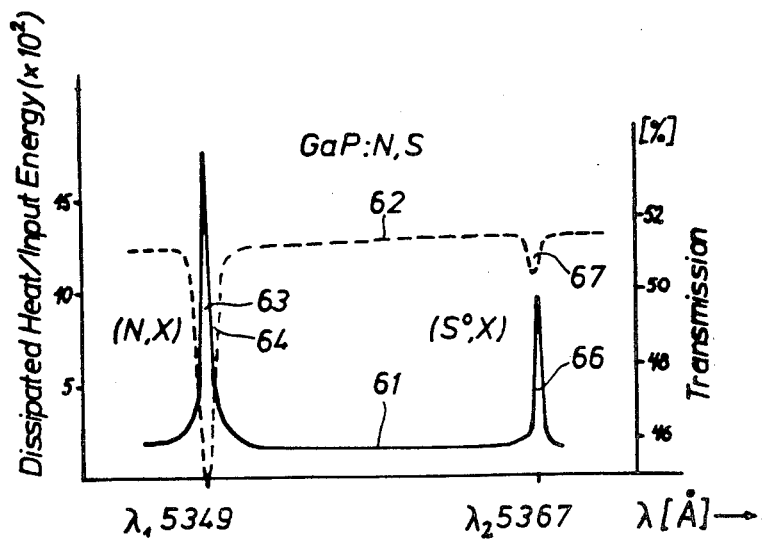
FIG. 4 is a graph showing the use of the method according to the invention to determine quantum yields and lifetimes of centers which recombine with and without radiation.

Finally, with reference to the drawing in FIG. 4, we shall describe a way of working the method according to the invention which makes it possible in many applications of practical significance to determine in simple fashion the quantum yield μ as well as the lifetime $\tau_r$ of radiant recombination (and $\tau_{nr}$ for nonradiant recombination) for an impurity center in a solid which can be excited by resonant irradiation, if a second center which can be excited in a resonant fashion is simultaneously present, which recombines solely by phonon emission, i.e., without radiation.

Let us assume that out example is GaP:NS, doped with nitrogen and sulfur.

Solid line 61 in FIG. 4 represents the CAS spectrum recorded at 1.5 K. for this system, using wavelength λ as the abscissa and the heat W developed in the sample by phonon emission as the ordinate, W being linked by relationship $$W = Q(1 - \mu) \qquad (7)$$

to the energy Q absorbed by the sample according to relationship (2) and the quantum yield μ for radiant recombination. Curve 62, shown dashed, is the transmission spectrum of the GaP:NS system at a temperature of 4 K.

CAS spectrum 61 has a pronounced peak 63 at wavelength $\lambda_1 = 5349$ Å, which is associated with the exciton (N, X) associated with the nitrogen impurity. This peak 63 corresponds to the sharp minimum 64 in transmission spectrum 62. This impurity center recombines with resonant excitation both by photon emission and by phonon emission, i.e., with and without radiation.

In addition, CAS spectrum 61 has a much less pronounced peak 66 at wavelength $\lambda_2$, which is associated with absorption caused by the ($S^o$, X) exciton associated with sulfur doping. This peak 66 in the CAS' spectrum 61 corresponds to the transmission minumum 67 in transmission spectrum 62, which is much weaker than transmission minimum 64.

Evaluation of the transmission spectrum reveals that the ($S^o$, X) exciton absorbs 1/6 of the energy that the (N, X) exciton absorbs.

Simple evaluation of the CAS spectrum reveals that the energy expended in zero-radiation recombination of the (N, X) exciton is twice as great as the heat generated by the zero-radiation recombination of the ($S^o$, X) exciton. It is also known of the ($S^o$, X) exciton that it recombines exclusively without radiation.

Now the quantum yield $\mu$ of the (N, X) center can be determined directly, which, by comparison with the ($S^o$, X) center absorbs six times the amount of light energy but gives off only twice the amount of nonradiation recombination, so that a quantum yield $\mu$ of $\frac{2}{3}$ or approximately 67% is obtained for the (N, X) exciton from a comparison of the CAS spectrum 61 with transmission spectrum 62.

The immediately apparent advantage of this method, which is always possible when a reference center is present, which recombines exclusively or for the most part by phonon emission, consists in the fact that in such cases no absolute calibration of the calorimeter is required.

If the quantum yield $\mu$ is determined in this way, and the total lifetime $\tau_t$ of the center in question is known from an additional measurement of the decay of the radiation recombination, i.e., luminescence, e.g., of the (N, X) center, the lifetime being linked by the relationship $$\tau_t^{-1} = \tau_r^{-1} + \tau_{nr}^{-1} \tag{8}$$

with the lifetime $T_r$ of the radiant recombination and lifetime $T_{nr}$ of the nonradiant recombination, since $$\mu = \tau_t/\tau_r \tag{9}$$

the lifetimes $\tau_r$ and $\tau_{nr}$ of radiant and nonradiant recombination can be determined in simple fashion.

We claim:

1. Method of calorimetric absorption spectroscopy, wherein a sample is irradiated with a measuring-light pulse of a specific power, duration, and wavelength, and the absorbance of a sample at the corresponding wavelength of the measuring light is determined from the heating of the sample which occurs as a consequence of absorption of a portion of the measuring light, characterized by the fact that the sample is held at a temperature at which its specific heat is only a small fraction of the value given at normal temperature (300 K.).

2. Method according to claim 1, characterized by the fact that the sample is cooled to a temperature between 1.5 K. and 0.3 K.

3. Method according to claim 1 or claim 2, characterized by the fact that, during a time interval which begins with the start of the irradiating light pulse and ends after a space of time which corresponds to five to 15 times the duration $\Delta t$ of the measuring-light pulse, the temperature rise and fall occurring during irradiation and after decay of the measuring-light pulse is recorded and a value $T_{max}$ characteristic of the maximum sample temperature is determined from this temperature curve.

4. Method according to claim 3, characterized by the fact that the sample temperature is determined from the change in resistance of an NTC resistor which is in good thermal contact with the sample, especially a carbon film resistor, said resistor having a resistance which increases inversely with temperature.

5. Method according to claim 3 characterized by the fact that the sample receives a specific amount of heat for absolute calibration of the resultant temperature curves within the framework of a reference measurement, and the temperature curve response resulting from this addition of heat is recorded, and the absolute calibration is obtained from a comparison with the temperature curves that result from radiation absorption.

6. Method according to claim 5, characterized by the fact that the application of the specific amount of heat is accomplished by applying a current of a specific magnitude and duration to a heating resistor which is in good thermal contact with the sample.

7. Method according to claim 3, characterized by its additional application to samples which have a first impurity center which is capable of recombination both with and without radiation, as well as a second recombining center which recombines by phonon emission alone, i.e., without radiation, if the total lifetime $\tau_t$ of the center which recombines both with and without radiation as well as the ratio between the quantities of exciting light power which can be absorbed by the two centers is known.

8. Method according to claim 1, characterized by its additional application to samples which have a first impurity center which is capable of recombination both with and without radiation, as well as a second recombining center which recombines by phonon emission alone, i.e., without radiation, if the total lifetime $\tau_t$ of the center which recombines both with and without radiation as well as the ratio between the quantities of exciting light power which can be absorbed by the two centers is known.

9. Method according to claim 1, characterized by the fact that the sample receives a specific amount of heat for absolute calibration of the resultant temperature curves within the framework of a reference measurement, and the temperature curve response resulting from this addition of heat is recorded, and the absolute calibration is obtained from a comparison with the temperature curves that result from radiation absorption.

10. A calorimetric absorption spectroscopy device, wherein a sample is irradiated with a measuring-light pulse of a specific power, duration, and wavelength, and the absorbance of a sample at the corresponding wavelength of the measuring light is determined from the heating of the sample which occurs as a consequence of absorption of a portion of the measuring light, comprising a helium cryostat for cooling the sample to a temperature between 1.5 K. to 0.3 K., wherein the cryostat has a heat-insulated cooling chamber for containing the sample, said chamber having an entrance window for the measuring light used to irradiate the sample, characterized by the fact that a temperature sensor is provided to detect the sample temperature, is mounted inside said cooling chamber and is shielded by a radiation shield against the incident measuring radiation, as well as the scattered radiation resulting from the latter.

11. Device according to claim 10, wherein said cryostat has a helium bath and a sample holder, the sample holder being in the form of a metal plate of good heat conductance, said plate being in direct thermal contact with the helium bath of the cryostat, whereby the sample is held against one side of the plate with only weak thermal coupling, and the temperature sensor is held against the side of the plate facing away from the sample, likewise with only poor thermal coupling to the sample holder, and whereby the thermal contact between the temperature sensor and the sample is provided by a copper wire with good heat conductance, said wire extending to the sample through an opening in the sample holder plate.

* * * * *